United States Patent [19]
Kelley et al.

[11] Patent Number: 5,708,033
[45] Date of Patent: Jan. 13, 1998

[54] AMIDE DERIVATIVES AND THEIR THERAPEUTIC USE

[75] Inventors: James Leroy Kelley; David Lee Musso, both of Raleigh, N.C.

[73] Assignee: Glaxo Wellcome Inc., Research Triangle Park, N.C.

[21] Appl. No.: 732,476

[22] PCT Filed: May 9, 1995

[86] PCT No.: PCT/GB95/01040

§ 371 Date: Nov. 8, 1996

§ 102(e) Date: Nov. 8, 1996

[87] PCT Pub. No.: WO95/30645

PCT Pub. Date: Nov. 16, 1995

[30] Foreign Application Priority Data

May 10, 1994 [EP] European Pat. Off. ............. 94303350

[51] Int. Cl.$^6$ .................. A61K 31/165; C07C 233/08; C07C 59/11; C07C 59/64

[52] U.S. Cl. ................. 514/617; 514/622; 564/180; 564/142; 564/139; 564/134; 562/405; 568/327

[58] Field of Search ............... 564/180, 172, 564/139, 142; 514/617, 622; 562/405, 466; 568/327, 323, 316

[56] References Cited

U.S. PATENT DOCUMENTS

| | | | |
|---|---|---|---|
| 3,312,730 | 4/1967 | Winter et al. | 514/617 |
| 3,923,866 | 12/1975 | Sawa et al. | 562/405 |
| 4,018,817 | 4/1977 | Noguchi et al. | 564/180 |
| 4,172,093 | 10/1979 | Goransson-Dahlander et al. | 544/230 |
| 5,416,118 | 5/1995 | Clader et al. | 514/617 |

FOREIGN PATENT DOCUMENTS

A94/26693  11/1994  WIPO.

OTHER PUBLICATIONS

A.G. Anderson et al., "The Synthesis of Dicyclopenta[ef,k] Heptalene(Azupyrene).I.", Journal of Organic Chemistry, 20 Apr. 1973, vol. 38, No. 8, pp. 1439-1444.

Lahiri et al, "Synthesis and Pharmocology of Some Indanamines", CA 69:35792, (1968).

Gruber et al, "Ara aliphatic Hydrocarbons, Orientation of Bromonation of Higher Bi- and Tricyclic Benzocycloalkanes", CA 99:194593, 1983.

Mukhopadhyay et al, "Studies on Antiinflammatory Activity Among a Series of Substituted Indan Acids", CA 104:199764, 1986.

Kelley et al, "Preparation of Indanylideneacetamide, Tetrahydronapthyl-ideneacetamides . . . ", CA 122: 265046, 1995.

*Primary Examiner*—Deborah Lambkin
*Attorney, Agent, or Firm*—Shah R. Makujina; Robert T. Hrubiec

[57] ABSTRACT

A compound of formula (I), wherein $R^1$ and $R^2$ are independently selected from chloro, fluoro, bromo, $C_{1-6}$ alkyl, $C_{1-6}$ alkoxy or $C_{1-6}$ haloalkyl provided that both $R^1$ and $R^2$ are not fluoro; $R^3$ and $R^4$ are independently selected from hydrogen and $C_{1-6}$ alkyl, and pharmaceutically acceptable salts, solvates or physiologically functional derivatives thereof, their use in medicine, particularly the phrophylaxis or treatment of conditions associated with inflammation, arthritis, or pain, pharmaceutical compositions comprising them, and processes for their preparation are disclosed.

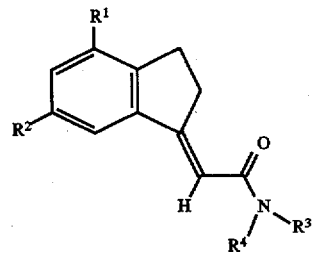

9 Claims, No Drawings

AMIDE DERIVATIVES AND THEIR THERAPEUTIC USE

This appln is a 371 of PCT/GB55/01040 May 9, 1995.

The present invention relates to a group of substituted carbocyclic amides, to pharmaceutical compositions which contain them, to methods for their preparation and their use in therapy, in particular in the treatment of inflammatory conditions.

We have found that a novel group of substituted carbocyclic amides have beneficial anti-inflammatory and analgesic properties. These compounds are relatively free of other pharmacological properties.

Accordingly, the present invention provides a compound of the formula (I):

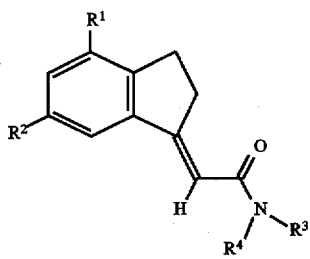

or a pharmaceutically acceptable salt, solvate or physiologically functional derivative thereof, wherein $^1$ and $R^2$ are the same or different and each is chloro, fluoro, bromo, $C_{1-6}$ alkyl, $C_{1-6}$ alkoxy or $C_{1-6}$ haloalkyl provided that $R^1$ and $R^2$ are not both fluoro;

$R^3$ and $R^4$ are independently selected from hydrogen and $C_{1-6}$ alkyl.

Suitably $R^1$ and $R^2$ are independently selected from chloro, fluoro, bromo or $C_{1-4}$ alkyl; preferably chloro, fluoro, bromo or methyl. Particularly preferred compounds of formula (I) include those wherein at least one of $^1$ and $R^2$ is chloro. Most preferably $R^1$ is chloro and $R^2$ is chloro, fluoro, bromo or methyl.

Preferably at least one of $R^1$ and $R^2$ is chloro.

Suitably $R^3$ and $R^4$ are independently selected from hydrogen or $C_{1-4}$ alkyl; preferably hydrogen, methyl or ethyl.

A preferred group of compounds of the formula (I) is that of the formula (IA):

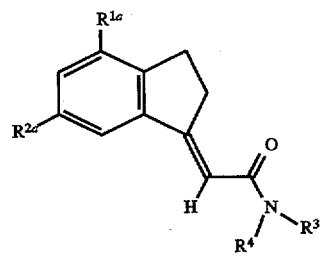

or a pharmaceutically acceptable salt, solvate or physiologically functional derivative thereof, wherein $R^{1a}$ is chloro, $R^{2a}$ is chloro, fluoro, bromo or methyl, $R^3$ and $R^4$ are the same or different and each is hydrogen, methyl or ethyl.

Preferred compounds of the present invention include:

(E)-2-(4-chloro-6-fluoro-1-indanylidene)-N-methylacetamide (E)-2-(4-chloro-6-fluoro-1-indanylidene)acetamide (E)-2-(4,6-dichloro-1-indanylidene)acetamide (E)-2-(6-fluoro-4-methyl-1-indanylidene)acetamide (E)-2-(6-fluoro-4-methyl-1-indanylidene)-N-methylacetamide (E)-2-(6-chloro-4-fluoro-1-indanylidene)acetamide (E)-2-(4-bromo-6-fluoro-1-indanylidene)acetamide (E)-2-(4-chloro-6-methyl-1-indanylidene)acetamide or a pharmaceutically acceptable salt thereof.

As used herein the term:

a) "$C_{1-6}$ alkyl" means an alkyl group having from 1 to 6 carbon atoms containing straight, branched chain or cyclic alkyl groups. Such alkyl groups preferably have 1 to 3 carbon atoms and are more preferably methyl, ethyl, propyl, prop-2-yl, butyl, but-2-yl, 2-methylprop-2-yl cyclopropyl or cyclobutyl. Alkyl groups are most preferably methyl or ethyl, or cyclopropyl.

b) "$C_{1-6}$ alkoxy" as a group or part of a group means a monovalent straight or branched chain radical having from 1 to 6 carbon atoms which are attached to the parent moiety through an oxygen atom. Such alkoxy groups preferably have 1 to 4 carbon atoms and are more preferably methoxy or ethoxy, most preferably methoxy.

c) "haloalkyl" means alkyl substituted by 1 to 5 fluoro or chloro atoms preferably fluoro atoms.

d) "physiologically functional derivatives" means any other physiologically acceptable derivative of a compound of the present invention, for example an ester, which, upon administration to the recipient, such as a human, is capable of providing (directly or indirectly) the said compound or an active metabolite or residue thereof.

e) "salt" means base salts as further defined herein below.

f) "solvate" means a combination, in definite proportions, of a compound of the present invention with its solvent.

It will be appreciated that the compounds of formula (I) can exist in various geoisomeric forms and as mixtures thereof in any proportions. The present invention includes within its scope such geoisomeric forms or mixtures of geoisomers, including the individual E and Z isomers of the compounds of formula (I) as well as mixtures of such isomers, in any proportions. Preferred compounds of formula (I) are those wherein the group adjacent to the exo double bond and the carbonyl group are on opposite sides of the exo double bond. The compounds of formula (I) may exist in forms wherein one or more carbon centres is/are chiral. The present invention includes within its scope each possible optical isomer substantially free, i.e., associated with less than 5%, of any other optical isomer(s), as well as mixtures of one or more optical isomers in any proportion, including racemic mixtures thereof.

Pharmaceutically acceptable salts are within the scope of the invention and are particularly suitable for medical applications because of their greater aqueous solubility relative to the parent (i.e., basic) compounds. Such salts must clearly have a pharmaceutically acceptable anion or cation. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are also within the scope of the invention as useful intermediates for the preparation or purification of pharmaceutically acceptable salts and/or for use in non-therapeutic, for example, in vitro, applications.

The compounds of formula (I) can also be used in the treatment of inflammatory and arthritic conditions, including rheumatoid arthritis, rheumatoid spondylitis, osteoarthritis, gouty arthritis, as well as non-articular inflammatory conditions, including herniated/ruptured/prolapsed intervertebral disk syndrome, bursitis, tendinitis, tenosynovitis, fibromyalgia syndrome and other inflammatory conditions associated with ligamentous sprain and regional musculoskeletal strain. It is particularly noted that compounds of formula (I) exhibit reduced occurrence of ulcerogenicity, as compared with other anti-inflammatory agents, such as ibuprofen, naproxen or aspirin.

The analgesic activity of compounds of formula (I) make them useful to control pain, e.g., pain associated with inflammation and/or trauma. Accordingly, compounds of the invention have use as mild and strong analgesics.

In further aspects, the present invention includes:

(a) compounds of formula (I) and pharmaceutically acceptable salts, solvates or physiologically functional derivatives thereof for use in medicine, particularly in the prophylaxis or treatment of clinical conditions associated with inflammation, arthritis or pain.

(b) pharmaceutical compositions comprising a compound of formula (I) or pharmaceutically acceptable salts, solvates, or physiologically functional derivatives thereof, and a pharmaceutically acceptable carrier therefor and optionally other therapeutic ingredients.

(c) a method for the treatment or prophylaxis of conditions associated with inflammation, arthritis or pain in a host, for example, a mammal including a human, comprising administering to the host an effective treatment amount of a compound of formula (I).

(d) use of a compound of formula (I) in the manufacture of a medicament for the treatment or prophylaxis of conditions associated with inflammation, arthritis or pain.

(e) processes for the preparation of compounds of formula (I) and intermediates therefor (including salts, solvates or physiologically functional derivatives thereof as defined herein).

The compounds according to the invention can also be employed in combination with other therapeutic agents for the treatment of conditions associated with inflammation, arthritis and/or pain. Examples of such other therapeutic agents include analgesics, such as codeine, oxycodone, acetaminophen, phenacetin, or ibuprofen; anti-arthritics, such as methotrexate or azathioprine; and decongestants, such as ephedrine or pseudoephedrine.

The pharmaceutical compositions of the compounds of formula (I), also referred to herein as active ingredients, may be administered for therapy by any suitable route including oral, rectal, nasal, topical (including buccal and sublingual), vaginal and parenteral (including subcutaneous, intramuscular, intravenous and intradermal). It will also be appreciated that the preferred route will vary with the conditions and age of the recipient, the nature of the disorder and the chosen active ingredient.

The amount required of the individual active ingredient for the treatment of, for example, increased muscle tone, inflammation, arthritis, and/or pain of course depends upon a number of factors including the severity of the condition to be treated and the identity of the recipient and will ultimately be at the discretion of the attendant physician.

In general, for the foregoing conditions a suitable dose of a compound of formula (I) or salts, solvates or physiologically functional derivatives thereof (estimated as the parent compound) is in the range of 0.05 to 100 mg per kilogram body weight of the recipient per day, preferably in the range of 0.1 to 50 mg per kilogram body weight per day, most preferably in the range 0.5 to 20 mg per kilogram body weight per day and optimally 1 to 10 mg per kilogram body weight per day. The desired dose is preferably presented as two, three, four, five, six or more sub-doses administered at appropriate intervals throughout the day. These sub-doses may be administered in unit dosage forms, for example, containing 1 to 1500 mg, preferably 5 to 1000 mg, and most preferably 10 to 700 mg of active ingredient per unit dosage form.

While it is possible for the active ingredient to be administered alone it is preferable to present it as a pharmaceutical composition. The compositions of the present invention comprise at least one active ingredient, as defined above, together with one or more acceptable carriers therefor and optionally other therapeutic agents. Each carrier must be "acceptable" in the sense of being compatible with the other ingredients of the composition and not injurious to the recipient.

Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by any methods well known in the an of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, cachets or tablets each containing a predetermined amount of the active ingredient: as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example hydroxypropylmethyl cellulose in varying proportions to provide the desired release profile. Tablets may optionally be provided with an enteric coating, to provide release in parts of the gut other than the stomach.

Compositions suitable for oral use as described above may also include buffering agents designed to neutralise stomach acidity. Such buffers may be chosen from a variety of organic or inorganic agents such as weak acids or bases admixed with their conjugated salts.

Compositions suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions for rectal administration may be presented as a suppository with a suitable base comprising for example cocoa butter or a salicytate.

Compositions suitable for vaginal administration may be presented as pessaries, tampons, creams, gels pastes, foams or spray formulations containing in addition to the active ingredient such carriers as are known in the art to be appropriate.

Compositions suitable for parenteral administration include aqueous and non-aqueous isotonic sterile injections solutions which may contain anti-oxidants, buffers, bacteriostats and solutes which render the compositions isotonic with the blood of the intended recipient; and aqueous and non-aqueous sterile suspensions which may include suspending agents and thickening agents, as liposomes or other microparticulate systems which are designed to target the compounds to blood components or one or more organs. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compositions suitable for transdermal administration may be presented as discrete patches adapted to remain in intimate contact with the epidermis of the recipient for a prolonged period of time. Such patches suitably contain the active compound as an optionally buffered, aqueous solution of, for example, 0.1 to 0.2M concentration with respect to the said compound. As one particular possibility, the active compound may be delivered from the patch by iontophoresis as generally described in *Pharmaceutical Research*, 3(6), 318 (1986).

Preferred unit dosage compositions are those containing a daily dose or unit, daily sub-dose, as herein above recited, or an appropriate fraction thereof, of an active ingredient.

It should be understood that in addition to the ingredients particularly mentioned above the compositions of this invention may include other agents conventional in the art having regard to the type of composition in question, for example, those suitable for oral administration may include such further agents as sweeteners, thickeners and flavouring agents.

The compounds of the invention can be prepared in any conventional manner and in accordance with the present invention, can, for example, be prepared by any method hereinafter described.

Thus, the present invention further includes a process for the preparation of compounds of formula (I) and salts, solvates and physiologically functional derivatives thereof which comprises:

reacting a compound of the formula (II):

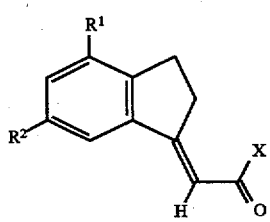

with an amine $NHR^3R^4$ wherein $R^1$ to $R^4$ are as hereinbefore defined and X is a leaving group.

Suitable leaving groups include halogen atoms such as chlorine or bromine, activated esters (e.g., N-hydroxysuccinimide, pentafluorophenyl, nitrophenyl, 1-hydroxybenzotriazole), mixed anhydrides (e.g., ethoxycarbonyloxy) or $C_{1-6}$ alkoxy (for example, ethoxy) groups.

Suitably the reaction is carried out in an inert solvent, e.g. a halogenated alkane such as dichloromethane, at a non-extreme temperature, e.g. $-20°$ C. to $120°$ C. and preferably at $0°$ C. to $30°$ C.

When $R^3$ and $R^4$ are hydrogen the compound $HNR^3R^4$, i.e. $NH_3$, is preferably used in the hydrated form as ammonium hydroxide and X is a halogen atom.

Compounds of formula (II) wherein X is a halogen atom can be prepared from compounds of formula (III)

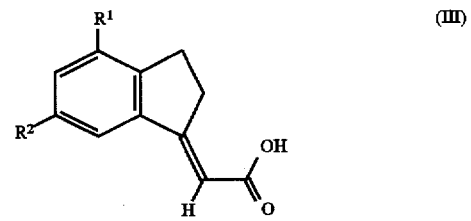

(wherein $R^1$, $R^2$ and $R^5$ are as hereinbefore defined) by reaction with a halogenating agent (e.g., oxalyl chloride, or thionyl chloride) in a suitable organic solvent (e.g., benzene, toluene, dichloromethane) optionally in the presence of a catalyst (for example DMF) at a temperature of about $-20°$ C. to the reflux temperature.

Compounds of formula (II) wherein X is alkoxy (e.g., ethoxy) can be prepared from compounds of formula (III) by reaction with a suitable polar solvent (e.g., an organic alcohol such as ethanol) optionally in the presence of a catalytic amount of an acid (e.g., tosic acid) at a temperature of about $0°$ C. to the reflux temperature.

Compounds of formula (II) wherein X is an activated ester (as described hereinbefore) can be prepared from compounds of formula (III) by reaction with the phenol or N-hydroxy compound and a carbodiimide (e.g., dicyclohexylcarbodiimide or 1-(3-imethylaminopropyl)-3-ethytcarbodiimide) in a solvent such as dimethylformamide (DMF) or dichloromethane at $0°$ C. to $50°$ C.

Compounds of formula (II) wherein X is an activated ester can be prepared from compounds of formula (III) by reaction with an alkylhaloester, e.g. ethylchloroformate in a suitable solvent such as tetrahydrofuran at a suitable temperature, e.g. $0°$ C. to room temperature.

Compounds of formula (I) can be prepared directly from compounds of formula (III) by reaction with a suitable coupling reagent (e.g., dicyclohexylcarbodiimide (DCC) or ethyl chloroformate) followed by reaction of the activated ester thus formed (without isolating this) with the appropriate amine, $HNR^3R^4$.

Compounds of formula (III) can be prepared by dehydration of compounds of formula (IV)

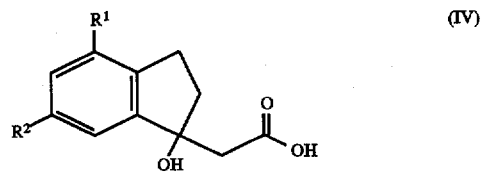

(wherein $R^1$ and $R^2$ are as hereinbefore defined) by reaction with an appropriate dehydrating agent (e.g., an acid such as trifluoroacetic acid) in a suitable organic solvent (e.g., dichloromethane) at a temperature of about $-20°$ C. to the reflux temperature.

Compounds of formula (IV) can be prepared by saponification of the corresponding $C_{1-6}$ alkyl ester, e.g. ethyl, with a base (e.g., sodium hydroxide) in a suitable polar solvent (e.g., ethanol) at a temperature of about $0°$ C. to the reflux temperature or with an aqueous acid (e.g., hydrochloric acid) at a temperature of about 0° C. to the reflux temperature.

The alkyl esters of compounds of formula (IV) can be prepared from compounds of formula (C)

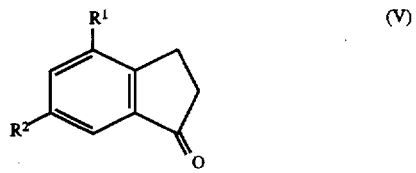

(wherein R¹ and R² are as hereinbefore defined) by reaction with X¹CH₂C(O)OR⁵ (wherein X¹ is a halogen atom such as chlorine, bromine, or iodine (preferably bromine)), R⁵ is $C_{1-6}$ alkyl, preferably ethyl, in the presence of a metal (e.g., zinc, preferably activated zinc) and a catalytic amount of halogen (e.g., iodine) in a suitable organic solvent (e.g., ethyl ether, benzene) at a temperature of about 0° C. to the reflux temperature or by reaction with the lithium salt of ethyl acetate in a suitable solvent (e.g., tetrahydrofuran) at a temperature between -100° C. to room temperature (e.g., -78° C.).

Compounds of formula (V) can be prepared from compounds of formula (VI)

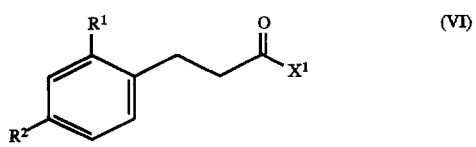

wherein R¹, R² and X¹ are as hereinbefore defined, by cyclization in the presence of a Lewis acid (e.g., aluminium chloride) in a suitable solvent (e.g., dichloromethane) at a temperature of about 0° C. to the reflux temperature.

Compounds of formula (VI) can be prepared from the corresponding acid by reaction with a halogenating agent (e.g., oxalyl chloride or thionyl chloride) either neat or in a suitable organic solvent (e.g. methylene chloride or N,N-dimethylformamide) at a temperature of about 0° C. to the reflux temperature.

The acids can be prepared (i) by saponification of the corresponding $C_{1-6}$ alkyl esters with a base (e.g., sodium hydroxide) in a suitable polar solvent (e.g., water or ethanol) at a temperature of about 0° C. to the reflux temperature or with an aqueous acid (e.g., hydrochloric acid) at a temperature of about 0° C. to the reflux temperature.

The $C_{1-6}$ alkyl esters can be prepared by catalytic hydrogenation of the corresponding $C_{1-6}$ alkyl acrylic esters in a suitable solvent (e.g., 95% ethanol) and a catalyst (e.g., platinum oxide) at ambient temperature under one to four atmospheres of hydrogen gas.

The acrylic esters can be prepared by reaction of a compound of formula (VII)

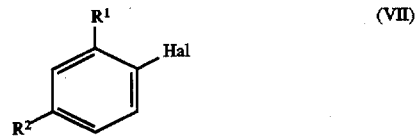

wherein R¹ and R² are as hereinbefore defined and Hal is a leaving group (e.g., Br, I or OSO₂CF₃) with $C_{1-6}$ esters of acrylic acid (preferably ethyl acrylate) in a suitable solvent (e.g., acetonitrile or dimethylformamide) in the presence of a catalyst (e.g., palladium(II)acetate/tri-o-tolyl phosphine or bis(triphenylphosphine)palladium(II)chloride) and a tertiary amine (e.g., triethylamine).

Compounds of formula (VII) wherein Hal is Br or I can be obtained commercially or prepared by methods well known to those skilled in the art or obtainable from the literature.

Compounds of formula (VII) wherein Hal is OSO₂CF₃ can be prepared from the corresponding phenol by reaction with trifluoromethanesulphonic anhydride in a suitable solvent (e.g., dichloromethane) in the presence of a base (e.g., pyridine). The phenols can be obtained commercially or prepared by methods well known to those skilled in the art or obtainable from the literature.

(ii) by catalytic hydrogenation of the corresponding acrylic acids in a suitable solvent (e.g., 95% ethanol) and catalyst (e.g., platinum oxide) at ambient temperature under one to four atmospheres of hydrogen gas.

The acrylic acids can be prepared from the corresponding aldehydes by reaction with malonic acid in a suitable solvent (e.g., pyridine) in the presence of a suitable base (e.g., piperidene).

The aldehydes can be obtained commercially or prepared by methods known to those skilled in the art or obtainable from the chemical literature.

(iii) from compounds of formula (VIII)

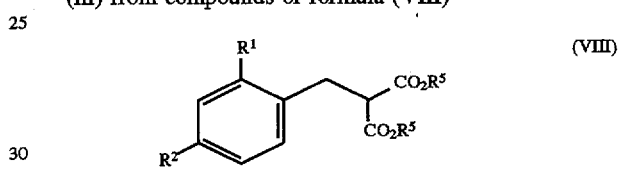

wherein R¹, R² and R⁵ are as hereinbefore defined, by reaction with strong base (e.g., aqueous potassium hydroxide) at the reflux temperature, followed by treatment with strong acid (e.g., H₂SO₄) at reflux temperature.

Compounds of formula (VIII) can be prepared by reacting a compound of formula (IX) with a compound of formula (VII)

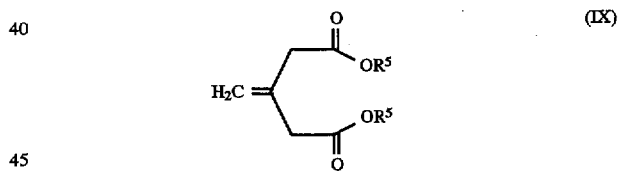

wherein R¹, R² and R⁵ are as hereinbefore defined in an organic solvent (e.g., anhydrous diethyl ether) and optionally in the presence of a copper halide (e.g., copper (I) iodide) at a temperature of between -50° C. to the reflux temperature.

Compounds of formula (IX) can be prepared by reacting a compound of formula (X) with formaldehyde

wherein R⁵ is as hereinbefore defined in an organic solvent (e.g., ethyl ether or dichloromethane, at a temperature of between room temperature and the reflux temperature.

Compounds of formula (X) can be obtained commercially or by techniques well known to those skilled in the an or readily obtainable from the chemical literature.

Alternatively, compounds of formula (I) can be prepared by reacting R³R⁴NC(O)CH₂ PO(OR⁶)₂ (wherein R³ and R⁴ are as hereinbefore defined) and R⁶ is $C_{1-6}$ alkyl with a base (e.g., NaH) in a suitable organic solvent (e.g., THF or DMSO) and reacting the resultant anionic species with a compound of formula (V) at a temperature of about 0° C. to the reflux temperature. The addition of an anionic stabilising reagent (e.g., potassium hexamethyldisilizane or a crown ether (e.g., 15-crown-5) can aid the reaction.

The compound $R^3R^4NC(O)CH_2PO(OR^6)_2$ can, depending on $R^3$ and $R^4$, be obtained commercially or by methods well known to those skilled in the art or readily obtainable from the chemical literature. Alternatively, these compounds can be prepared by reacting the appropriate $R^3R^4NC(O)CH_2X$ (wherein X is a halogen atom) with the appropriate $P(OR^6)_3$ in a suitable organic solvent (e.g., THF) at a temperature of about 0° C. to 50° C.

The compound $R^3R^4NC(O)CH_2X$ can be prepared by reacting the appropriate amine $R^3R^4NH$ with $XCH_2C(O)X$ in a suitable organic solvent (e.g., diethyl ether) at a temperature of about 0° C. to the reflux temperature.

The compound $XCH_2C(O)X$ can be obtained commercially or by methods well known to those skilled in the art of preparing such compounds or readily obtainable from the chemical literature.

Alternatively, compounds of formula (I) can be prepared by reacting $R^3R^4NC(O)CH_2P^{(+)}(Ph)_3Cl^{(-)}$(wherein $R^3$ and $R^4$ are as hereinbefore defined and Ph is phenyl) with a suitable base (e.g., NaH) in a suitable organic solvent (e.g., dimethoxyethane) at a temperature of about 0° C. to 50° C., and reacting the resultant anionic species with a compound of formula (V) respectively at a temperature of about 0° C. to the reflux temperature.

The compound $R^3R^4NC(O)CH_2P^{(+)}(Ph)_3Cl^{(-)}$ can be prepared by reacting $R^3R^4NC(O)CH_2X$ with about a 50% molar excess of $P(Ph)_3$ (triphenylphosphine) in a suitable organic solvent (e.g., THF) at a temperature of about 20° C. to the reflux temperature.

The compounds of formula (I) as well as any of the intermediates used in the preparation of these compounds can be effected with one or more of the following optional conversions:

(i) converting a compound of formula (I) or intermediates thereof so formed into base salts, or other physiologically functional derivatives thereof;

(ii) when a base salt, or other physiologically functional derivative of a compound of formula (I) or an intermediate thereof is formed, converting the said salt or derivative into a compound of formula (I) or an intermediate thereof, or a different derivative thereof.

The present invention further includes novel intermediates which are of particular value for the preparation of certain compounds of formula. Accordingly, there are provided intermediates of formulae (II), (III) and (IV) as hereinbefore defined.

Novel intermediates which are of particular value include:
2-(4-chloro-6-fluoro-1-hydroxy-1-indanyl)acetic acid
(E)-2-(4-Chloro-6-fluoro-1-indanylidene)acetic acid
(E)-2-(4-Chloro-6-fluoro-1-indanylidene)acetyl chloride
2-(4,6-Dichloro-1-hydroxy-1-indanyl)acetic acid
(E)-(4,6-Dichloro-1-indanylidene)acetic acid
(E)-2-(4,6-Dichloro-1-indanylidene)acetyl chloride
2-(6-Fluoro-1-hydroxy-4-methyl-1-indanyl)acetic acid
(E)-2-(6-Fluoro-4-methyl-1-indanylidene)acetic acid
(E)-2(6-Fluoro-4-methyl-1-indanylidene)acetyl chloride
2-(6-Chloro-4-fluoro-1-hydroxy-1-indanyl)acetic acid
(E)-2-(6-Chloro-4-fluoro-1-indanylidene)acetic acid
(E)-2-(6-Chloro-4-fluoro-1-indanylidene)acetyl chloride
2-(4-Bromo-6-fluoro-1-hydroxy-1-indanylidene)acetic acid
(E)-2-(4-Bromo-6-fluoro-1-indanylidene)acetic acid
(E)-2-(4-Bromo-6-fluoro-1-indanyl)acetyl chloride
2-(4-Chloro-6-methyl-1-hydroxy-1-indanyl)acetic acid
(E)-2-(4-Chloro-6-methyl-1-indanylidene)acetic acid
(E)-2-(4-Chloro-6-methyl-1-indanylidene)acetyl chloride The following examples illustrate the present invention but should not be construed as a limitation to the scope thereof.

EXAMPLE 1

Preparation of (E)-2-(4-Chloro-6-fluoro-1-indanylidene)-N-Methylacetamide

Preparation of 2-Chloro-4-Fluorocinnamic acid

To a mixture of 2-chloro-4-fluorobenzaldehyde (20.0 g, 0.13 mol, Aldrich) and malonic acid (26.2 g, 0.25 mol, Aldrich) in pyridine (100 ml) at 50° C. was added dropwise piperidine (10 ml). After 18 h at 70° C., the mixture was poured into an ice cold solution of concentrated HCl (120 ml) and water (1.5 L). The resulting solid was filtered and washed repeatedly with water to give 24.4 g (96%) of 2-chloro-4-fluoro-cinnamic acid as a white solid: Recrystallization of 1.5 g from acetone:water mixtures gave 1.1 g of 2-chloro-4-fluorocinnamic acid as a white solid: mp 243°–245° C.

b) Preparation of 3-(2-Chloro-4-fluorophenyl)propanoic Acid

A mixture of 2-chloro-4-fluorocinnamic acid (22.9 g, 0.11 mol) and platinum oxide hydrate (0.5 g, EM Scientific) in 95% ethanol (140 ml) was placed on a Parr hydrogenation apparatus. After the appropriate amount of hydrogen was taken up, the catalyst was filtered and the mixture was concentrated in vacuo to give 22.6 g (98%) of 3-(2-chloro-4-fluorophenyl)propanoic acid as a purple solid. This material was used without further purification.

3a) 3-(2,4-dichlorophenyl)propanoic Acid was prepared in a similar manner to that described in Example 1b from 2,4-dichlorocinnamic acid (25.0 g, 0.12 mol, Aldrich). This material was used without further purification.

c) Preparation of 4-Chloro-6-fluoro-1-indanone

To a mixture of 3-(2-chloro-4-fluorophenyl)propanoic acid (21.6 g, 0.11 mol) and dichloromethane at room temperature was added dropwise oxalyl chloride (19.2 ml). The mixture was stirred at room temperature until gas evolution had ceased. The excess oxalyl chloride was removed by distillation to give 3-(2-chloro-4-fluorophenyl)propionyl chloride. A solution of the 3-(2-chloro-4-fluorophenyl) propionyl chloride in dichloromethane (100 ml) was added dropwise to a mixture of aluminium chloride (17.3 g, 0.13 mol, Aldrich) in dichloromethane (100 ml) at room temperature. After the addition was completed, the mixture was refluxed for 2.5 h. The reaction mixture was poured into ice water (1.5 L). The two phases were separated and the dichloromethane phase was washed with 0.1N aqueous sodium hydroxide, dried ($Na_2SO_4$), and concentrated to give crude 4-chloro-6-fluoro-1-indanone. Chromatography on silica gel with hexanes:dichloromethane (1:1) as eluent gave 11.1 g (55%) of 4-chloro-6-fluoro-1-indanone as a white solid: mp 94°–96° C.

3b) 4,6-dichloro-1-indanone was prepared in a similar manner to that described in Example 1c from 3-(2,4-dichlorophenyl) propanoic acid (24.3 g, 0.11 mol). Chromatography on silica gel with hexanes:dichloromethane (1:1) as eluent gave 12.2 g (55%) of 4,6-dichloro-1-indanone as a white solid. Recrystallization of 1.0 g from hexanes gave 0.7 g of 4,6-dichloro-1-indanone as a white solid: mp 118°–120° C.

d) Preparation of Ethyl 2-(4-Chloro-6-fluoro-1-hydroxy-1-indanyl)acetate

Ethyl acetate (5.9 g, 0.07 mol) was added dropwise to a stirred, chilled (dry ice-acetone bath) solution of lithium diisopropylamide (prepared by dropwise addition of a 2.5M solution of n-butyllithium (26.8 ml, 0.07 mol) in hexane to a chilled (dry ice-acetone bath) solution of diisopropylamine (6.8 g, 0.07 mol) in tetrahydrofuran (35 ml) ). After 30 min, a solution of 4-chloro-6-fluoro-1-indanone (12.4 g, 0.07 mol) in tetrahydrofuran (100 ml) was added dropwise and the mixture was stirred for 1 h (dry ice-acetone bath). A solution of ammonium chloride (10.6 g, 0.20 mol) in water (80 ml) was added and the mixture was allowed to come to ambient temperature. The aqueous phase was separated and extracted with diethyl ether. The combined organic phase was dried (sodium sulphate), filtered and concentrated in vacuo to give 19.5 g of crude ethyl 2-(4-chloro-6-fluoro-1-hydroxy-1-indanyl)acetate. Chromatography on silica gel with hexanes:ethyl acetate (8:2) as eluent gave 15.2 g (83%) of a yellow oil; NMR (DMSO-$d_6$): a 7.13–7.28 (m, 2H), 5.55 (s, 1H), 3.98 (m, 2H), 2.79 (2m's, 4H), 2.50 (m, 1H), 2.11 (m, 1H). 1.08 (t, 3H).

3c) Ethyl 2-(4,6-Dichloro-1-hydroxy-1-indanyl)acetate was prepared in a similar manner to that described in Example 1d from 4,6-dichloro-1-indanone. Chromatography on silica gel with hexanes:ethyl acetate (8:2) as eluent gave 10.6 g (65%) of a yellow oil; NMR (CDCl$_3$): δ7.22–7.27 (m, 2H), 4.28 (br, 1H), 4.21 (m, 2H), 3.03 (m, 1H), 2.75 (m,3H), 2.30 (m, 2H), 1.28 (t, 3H).

e) Preparation of 2-(4-Chloro-6-fluoro-1-hydroxy-1-indanyl)acetic Acid

A mixture of ethyl 2-(4-chloro-6-fluoro-1-hydroxy-1-indanyl)acetate (14.5 g, 0.05 mol), 1N sodium hydroxide (52 ml) and absolute ethanol (100 ml) was stirred for 18 h at room temperature. The mixture was concentrated in vacuo, diluted with H$_2$O and washed with diethyl ether. The aqueous phase was neutralised with 1.0N hydrochloric acid (52 ml) and extracted with diethyl ether. The diethyl ether extracts were dried over sodium sulphate, filtered and concentrated in vacuo to give 12.5 g (96%) of crude 2-(4-chloro-6-fluoro-1-hydroxy-1-indanyl)acetic acid. This material was used immediately without further purification.

3d) 2-(4,6-Dichloro-1-hydroxy-1-indanyl)acetic Acid was prepared in a similar manner to that described in Example 1e from ethyl 2-(4,6-dichloro-1-hydroxy-1-indanyl)acetate (9.9 g, 0.03 mol). This material was used immediately without further purification.

f) Preparation of (E)-2-(4-Chloro-6-fluoro-1-indanylidene)acetic Acid

Trifluoroacetic acid (27.4 ml) was added to a stirred, chilled (ice-methanol bath) solution of 2-(4-chloro-6-fluoro-1-hydroxy-1-indanyl)acetic acid (12.5 g, 0.05 mol) in dichloromethane (200 ml). After 1.5 h, the mixture was concentrated in vacuo. Dichloromethane was added to the residue and the mixture was concentrated in vacuo to give 10.6 g of crude (E)-2-(4-chloro-6-fluoro-1-indanylidene) acetic acid. Chromatography of a 1.0 g sample on silica gel with ethyl acetate:hexanes (1:1) as eluent gave 0.32 g of (E)-2-(4-chloro-6-fluoro-1-indanylidene)acetic acid as a white solid: mp 229°–230° C.

3e) (E)-2-(4,6-Dichloro-1-indanylidene)acetic Acid was prepared in a similar manner to that described in Example 1f from 2-(4,6-dichloro-1- hydroxy-1-indanyl)acetic acid (8.6 g, 0.03 mol). A 1.0 g sample was recrystallized from isopropanol:water mixtures to give 0.6 g of (E)-2-(4,6-dichloro-1-indanylidene)acetic acid as a white solid: mp 245°–247° C.

g) Preparation of(E)-2-(4-Chloro-6-fluoro-1-indanylidene)acetyl Chloride

A suspension of (E)-2-(4-chloro-6-fluoro-1-indanylidene) acetic acid (9.6 g, 0.04 mol) in dichloromethane (100 ml) was treated with oxalyl chloride (10.7 g, 0.08 mol) and allowed to stir at room temperature for 3 h. The resulting solution was concentrated in vacuo and the residue used without further purification.

3f) (E)-2-(4,6-dichloro-1-indanylidene)acetyl Chloride was prepared in a similar manner to that described in Example 1g from (E)-2-(4,6-dichloro-1-indanylidene) acetic acid (5.3 g, 0.02 mol). The resulting residue was used without further purification.

h) Preparation of (E)-2-(4-Chloro-6-fluoro-1-indanylidene)-N-Methylacetamide

A solution of (E)-2-(4-chloro-6-fluoro-1-indanylidene) acetyl chloride (4.0 g, 0.015 mol) in dichloromethane (36 ml) was added dropwise to an ice-cold mixture of 40% aqueous methylamine (2.6 ml, 0.03mol) and dichloromethane (100 ml) and the mixture was stirred at ambient temperature for 18 h. The reaction mixture was concentrated in vacuo and the residue was partitioned between 5% aqueous sodium bicarbonate and ethyl acetate. The ethyl acetate solution was dried over sodium sulphate, filtered and concentrated in vacuo. The residue was purified by column chromatography on silica gel using ethyl acetate:hexanes (1:1) as eluent to give 1.59 g (44%) of (E)-2-(4-chloro-6-fluoro-1-indanylidene)-N-Methylacetamide as a white solid: mp 173°–175° C.; NMR (CDCl$_3$): δ7.10–7.30 (m, 2H), 6.16 (s, 1H), 5.64 (br, 1H), 3.42–3.48 (m, 2H), 3.01–3.07 (m, 2H), 2.95 (s, 3H).

EXAMPLE 2

(E)-2-(4-Chloro-6-fluoro-1-indanylidene)acetamide

A solution of (E)-2-(4-chloro-6-fluoro-1-indanylidene) acetyl chloride (4.0 g, 0.015 mol) [as prepared in example 1 g] in dichloromethane (36 ml) was added dropwise to an ice-cold mixture of 30% aqueous ammonium hydroxide (2.0 ml, 0.03 mol) and dichloromethane (100 ml) and the mixture was stirred at ambient temperature for 18 h. The reaction mixture was concentrated in vacuo and the residue was partitioned between 5% aqueous sodium bicarbonate and ethyl acetate. The ethyl acetate solution was dried over sodium sulphate, filtered and concentrated in vacuo. The residue was purified by column chromatography on silica gel with ethyl acetate:hexanes (2:1) as eluent. Trituration of the resulting solid with pentane gave 1.47 g (43%) of (E)-2-(4-chloro-6-fluoro-1-indanylidene)acetamide as a white solid: m.p. 182°–184° C.

EXAMPLE 3

Preparation of (E)-2-(4,6-Dichloro-1-indanylidene) acetamide (E)-2-(4,6-Dichloro-1-indanylidene)acetamide was prepared from intermediate 3f in and analagous manner to that described in Example 2 The residue was purified by column chromatography on silica gel with ethyl acetate:hexanes (3:2) as eluent. Trituration of the resulting solid with pentane gave 1.01 g (52%) of (E)-2-(4,6-dichloro-1-indanylidene) acetamide as a white solid: m.p. 210°–212° C.

EXAMPLE 4

Preparation of (E)-2-(6-Fluoro-4-Methyl-1-indanylidene) acetamide (a) Preparation of(E)-Ethyl 3-(4-Fluoro-2-Methylphenyl) Acrylate A mixture of 2-bromo-5-fluorotoluene (17.6 g, 0.09 mol, Aldrich), ethyl acrylate (9.3 g 0.09 mol), triethylamine (9.4 g, 0.09 mol), Palladium(II) acetate (2.7 g, 0.01 mol) and tri-o-tolylphosphine (7.3 g, 0.02 mol) in acetonitrile (60 ml) was placed in a Parr bomb and heated at 110° C. for 12 h. After cooling to room temperature, the mixture was diluted with diethyl ether and filtered. The filtrate was concentrated in vacuo to get 33.0 g of an orange oil. Chromatography on silica gel using initially hexanes:dichloromethane (8:2) and subsequently hexanes:dichloromethane (6:4) as eluent gave 18.0 g (93%) of (E)-ethyl 3-(4-fluoro-2-methylphenyl) acrylate as a pale yellow solid: NMR (DMSO-$d_6$); $\delta$7.78 (d, 1H, CH=, J=16 Hz), 7.78 (m, 1H, ArH), 7.02–7.15 (m, 2H, Ar), 6.48 (d, 1H, CH=, J=16 Hz), 4.17 (q, 2H, CH$_2$), 2.38 (s, 3H, CH$_3$), 1.24 (t, 3H, CH$_3$).

b) Preparation of Ethyl 3-(4-Fluoro-3-Methylphenyl) Propionate

A mixture of (E)-ethyl 3-(4-fluoro-2-methylphenyl) acrylate (32.9 g, 0.16 mol) and platinum oxide hydrate (0.5 g, EM Scientific) in 95% ethanol (125 ml) was placed on a Parr apparatus. After the appropriate amount of hydrogen was taken up, the catalyst was filtered and the filtrate was concentrated in vacuo to give 33.7 g of ethyl 3-(4-fluoro-3-methylphenyl)propionate. A 1.0 g sample was purified by chromatography on silica gel with hexanes:dichloromethane as eluent to give 0.92 g of ethyl 3-(4-fluoro-3-methylphenyl) propionate as a colourless oil: NMR (CDCl$_3$); $\delta$6.78–7.26 (m, 3H, Ar), 4.13 (q, 2H, CH$_2$), 2.90 (t, 2H, CH$_2$), 2.54 (t, 2H, CH$_2$), 2.31 (s, 3H, CH$_3$), 1.24 (t, 3H CH$_3$).

c) Preparation of 3-(4-Fluoro-2-Methylphenyl) Propionic Acid

To a Mixture of ethyl 3-(4-fluoro-3-methylphenyl) propionate (32.7 g, 0.16 mol) in ethanol (150 ml) chilled to ice bath temperature was added in one portion 1.0N sodium hydroxide (156 ml) solution and the mixture was stirred for 18 h at room temperature. The mixture was concentrated in vacuo, the residue was dissolved in water, and the aqueous phase was washed with diethyl ether. The aqueous phase was chilled in an ice bath and made acidic by addition of 1.0N hydrogen chloride (160 ml) solution. Filtration of the resulting solid gave 25.8 g (91%) of 3-(4-fluoro-2-methylphenyl) propionic acid. An 0.5 g sample was recrystallized from water to give 0.26 g of 3-(4-fluoro-2-methylphenyl) propionic acid as a white solid: mp 112°–113° C.

d) Preparation of (E)-2-(6-Fluoro-4-Methyl-1-indanylidene)Acetamide

Prepared from (E)-2-(6-fluoro-4-methyl-1-indanylidene) acetyl chloride (4.0 g, 0.018 mol) according to the method described in Examples 1c–1g and 2 via the following intermediates:

(i) 6-Fluoro-4-methyl-1-indanone, white solid, mp 90°–92° C.

(ii) Ethyl 2-(6-Fluoro-1-Hydroxy-4-Methyl-1-Indanyl) Acetate, pale yellow oil, NMR (CDCl$_3$): $\delta$6.76–6.88 (m, 2H, Ar), 4.22 (q, 2H, CH$_2$CH$_3$), 2.79 (2m's, 4H, CH$_2$s), 2.30 (m, 2H, CH$_2$), 2.24 (s, 3H, CH$_3$), 1.28 (t, 3H, CH$_3$).

(iii) 2-(6-Fluoro-1-Hydroxy-4-Methyl-1-indanyl)Acetic Acid, used immediately without further purification.

(iv) (E)-2-(6-Fluoro-4-Methyl-1-Indanylidene)Acetic Acid. Recrystallization of 0.5 g from 2-propanol gave 0.23 g of (E)-2-(6-fluoro-4-methyl-1-indanylidene)acetic acid as a white solid: mp 243°–246° C.

(v) (E)-2-(6-Fluoro-4-Methyl-1-Indanylidene)Acetyl Chloride, used without further purification.

Chromatography on silica gel with ethyl acetate:hexanes (6:4) as eluent and trituration of the resulting solid with pentane gave 1.8 g (49%) of (E)-2-(6-fluoro-4-methyl-1-indanylidene)acetamide as an off-white solid: mp 178°–180° C.; NMR (DMSO-$d_6$): $\delta$7.25 (br s, 1H, NH$_2$), 7.07–7.11 (m, 1H, Ar), 6.99–7.03 (m, 1H, Ar), 6.84 (br s, 1H, NH$_2$), 6.34 (t, 1H, =CH), 3.15–3.20, 2.80–2.84 (2m's, 4H, 2XCH$_2$), 2.22 (s, 3H, CH$_3$)

EXAMPLE 5

Preparation of(E)-2-(6-Fluoro-4-Methyl-1-Indanylidene) -N-Methyl Acetamide

The above compound was prepared from (E)-2-(6-fluoro-4-methyl-1-indanylidene)acetyl chloride (4.0 g, 0.018 mol) by an analagous process to that described in Example 1h. The acetyl chloride was prepared as described in Example 1g. Chromatography on silica gel with ethyl acetate: hexanes (6:4) as eluent and trituration of the resulting solid with pentane gave 1.71 g (43%) of (E)-2-(6-fluoro-4-methyl-1-indanylidene)-N-methyl acetamide as an off-white solid: mp 202°–204° C.; NMR (DMSO-$d_6$): $\delta$7.78 (br d, 1H, NH), 7.07–7.11 (m, 1H, Ar), 6.99–7.02 (m, 1H, Ar), 6.31 (t, 1H, =CH), 3.17–3.22, 2.80–2.84 (2m's, 4H, 2XCH$_2$), 2.64 (d, 3H, CH$_3$), 2.22 (s, 3H, CH$_3$).

EXAMPLE 6

Preparation of(E)-2-(6-Chloro-4-Fluoro-1-indanylidene) acetamide a. Preparation of 4-Chloro-2-Fluorophenyl Trifluoromethanesulphonate A mixture of 4-chloro-2-fluorophenol (25.0 g, 0.17 mol, Aldrich) and pyridine (13.5 g, 0.17 mol, Aldrich) in dichloromethane (120 ml) was added dropwise to a solution of trifluoromethanesulphonic anhydride (50.0 g, 0.18 mol, Aldrich) in dichloromethane (120 ml) at ice bath temperature. After stirring at ambient temperature for 60 h, the reaction mixture was washed with water and dried over sodium sulphate, filtered, and concentrated in vacuo to give 45 g of crude 4-chloro-2-fluorophenyl trifluoromethanesulphonate. Chromatography on silica gel with hexanes as eluent gave 32.2 g (68%) of 4-chloro-2-fluorophenyltrifluoromethane sulphonate as a colourless oil: NMR (CDCl$_3$); $\delta$ 7.20–7.33 (m, 3H, Ar).

b) Preparation of(E)-Ethyl 3-(4-Chloro-2-Fluorophenyl) Acrylate

A mixture of 4-chloro-2-fluorophenyl trifluoromethanesulphonate (5.0 g, 0.02 mol), ethyl acrylate (1.8 g, 0.02 mol, Aldrich), triethylamine (1.8 g 0.02 mol), and bis (triphenylphosphine)palladium(II) chloride (1.4 g, 0.002 mol, Aldrich) in dimethyl formamide (20 ml) was placed in a Parr bomb and heated at 110° C. for 12 h. After cooling to ambient temperature, the mixture was diluted with diethyl ether and filtered. The filtrate was washed with water, filtered and concentrated in vacuo to get 6.6 g of an orange oil. Chromatography on silica gel using initially hexanes:dichloromethane (7:3) as eluent gave (a) 1.57 g of pure (E)-ethyl 3-(4-chloro-2-fluorophenyl) acrylate as a green oil which solidified on standing and (b) 0.93 g of (E)-ethyl 3-(4-chloro-2-fluorophenyl) acrylate containing a minor impurity. Recrystallization of(a) from acetone: water mixtures gave 0.82 g of(E)-ethyl 3-(4-chloro-2-fluorophenyl) acrylate as a white solid: mp 38°–40° C.

15 c) Preparation of 3-(4-Chloro-2-Fluorophenyl) Propionic Acid

The above compound was prepared from (E)-ethyl 3-(4-chloro-2-fluorophenyl) acrylate (37.9 g, 0.17 mol) according to the methods described in Examples 4b and 4c via the following intermediate:

(i) Ethyl 3-(4-chloro-2-fluorophenyl)propionate. A 1.0 g sample was purified by chromatography on silica gel with hexanes: ethyl acetate (98:2) as eluent to give 0.38 g of ethyl 3-(4-chloro-2-fluorophenyl) propionate as a colourless oil: NMR (CDCl$_3$); δ7.03–7.18 (m, 3H, Ar), 4.13 (q, 2H, CH$_2$), 2.93 (t, 2H, CH$_2$), 2.60 (t, 2H, CH$_2$), 1.23 (t, 3H CH$_3$).

A 0.5 g sample was recrystallized from water to give 0.18 g of 3-(4-chloro-2-fluorophenyl) propionic acid as a white solid: mp 83°–85° C.

d) Preparation of 6-Chloro-4-Fluoro-1-indanone

The above compound was prepared from 3-(4-chloro-2-fluorophenyl)propionic acid (8.4 g, 0.04 mol) by a method analagous to that described in Example 1c. Chromatography on silica gel with hexanes: methylene chloride (7:3) as eluent gave 4.1 g (54%) of 6-chloro-4-fluoro-1-indanone as a white solid: mp 105°–107° C.

e) Preparation of Ethyl 2-(6-Chloro-4-Fluoro-1-Hydroxy-1-Indanyl) Acetate

A solution of ethyl acetate (8.3 g, 0.09 mol) in tetrahydrofuran (10 ml) was added dropwise to a solution of lithium diisopropylamide (62.7 ml of a 1.5M solution in cyclohexane, 10.1 g, 0.09 mol, Aldrich) in tetrahydrofuran (100 ml) at −78° C. under a nitrogen atmosphere. After 30 min, a solution of 6-chloro-4-fluoro-1-indanone in tetrahydrofuran (175 ml) was added dropwise, and the mixture was stirred at −78° C. for 70 min. The reaction was quenched with a solution of ammonium chloride (15.1 g, 0.27 mol) in water (100 ml), and the reaction mixture was allowed to come to ambient temperature overnight. The phases were separated, and the aqueous phase was extracted with diethyl ether. The combined organic phase was dried (sodium sulphate), filtered, and concentrated in vacuo to give 24.4 g of crude ethyl 2-(6-chloro-4-fluoro-1-hydroxy-1-indanyl) acetate. Chromatography on silica gel using hexanes:ethyl acetate (9:1) as eluent gave 14.7 g (57%) of ethyl 2-(6-chloro-4-fluoro-1-hydroxy-1-indanyl) acetate as a yellow oil. Rechromatography of a 0.5 g sample on silica gel with dichloromethane as eluent gave 0.27 g of ethyl 2-(6-chloro-4-fluoro-1-hydroxy-1-indanyl)acetate as a colourless oil; NMR (CDCl$_3$): δ6.96–7.12 (m, 2H, Ar), 4.35 (br s, 1H, OH), 4.22 (q, 2H, CH$_2$CH$_3$), 3.04 (m, 1H, CH$_2$), 2.75 (2m's, 3H, CH$_2$'s), 2.32 (m, 2H, CH$_2$), 1.28 (t, 3H, CH$_3$).

f) Preparation of (E)-2-(6-Chloro-4-Fluoro-1-Indanylidene)Acetamide

The above compound was prepared from ethyl 2-(6-chloro-4-fluoro-1-hydroxy-1-indanyl) acetate (16.0 g, 0.06 mol) by methods analagous to those described in Examples 1e–1g and 2 via the following intermediates:

(i) 2-(6-chloro-4-fluoro-1-hydroxy-1-indanyl)acetic acid. Used without further purification.

(ii) (E)-2-(6-Chloro-4-Fluoro-1-Indanylidene)Acetic Acid. A 1.0 g sample was purified by column chromatography on Silica gel with hexanes:ethyl acetate (1:1) as eluent followed by recrystallization with 2-propanol to give 0.21 g of (E)-2-(6-chloro-4-fluoro-1-indanylidene)acetic acid as a white solid: mp 254°–256° C.

(iii) (E)-2-(6-Chloro-4-Fluoro-1-Indanylidene)Acetyl Chloride. Used without further purification.

Chromatography on silica gel with ethyl acetate: hexanes (7:3) as eluent and trituration of the resulting solid with

16 pentane gave 1.77 g (49%) of (E)-2-(6-chloro-4-fluoro-1-indanylidene)acetamide as a white solid: mp 171°–173° C.; NMR (DMSO-d$_6$): δ7.43 (d, 1H, Ar), 7.37 (dd, 1H, Ar), 7.31 (br s, 1H, NH$_2$), 6.99 (br s, 1H, NH$_2$), 6.46 (t, 1H, =CH), 3.17–3.22, 2.92–2.97 (2m's, 4H, 2XCH$_2$).

EXAMPLE 7

Preparation of (E)-2-(4-Bromo-6-Fluoro-1-indanylidene) acetamide a) Preparation of 2-Bromo-1-(Bromomethyl)-4-Fluorobenzene A mixture of 2-Bromo-4-Fluorotoluene (46.6 g, 0.25 mol, Aldrich), N-bromosuccinimide (46.3 g, 0.26 mol, Aldrich) and benzoyl peroxide (0.5 g, 0.002 mol, Aldrich) in carbon tetrachloride (500 ml) was refluxed and illuminated (250 watt, infrared lamp) for 18 h. After cooling to room temperature, the succinimide was filtered and the filtrate was concentrated in vacuo. Chromatography on silica gel with hexanes as eluent gave 41.8 g (62%) of 2-bromo-1-(bromomethyl)-4-fluorobenzene as a white solid: mp 47°–49° C.

b) Preparation of Diethyl 2-(2-Bromo-4-Fluorobenzyl) Malonate

A solution of diethyl malonate (25.9 g, 0.16 mol) in dimethoxyethane (10 ml) was added dropwise to a suspension of sodium hydride (6.0 g of a 60% dispersion in mineral oil, 0.15 mol, Aldrich) in dimethoxyethane (25 ml) at ambient temperature. After 1 h, a solution of 2-bromo-1-(bromomethyl)-4-fluorobenzene (40.8 g, 0.15 mol) in dimethoxyethane (125 ml) was added dropwise and the mixture was refluxed for 1.5 h. The reaction mixture was cooled to ambient temperature and concentrated in vacuo. The residue was partitioned between dichloromethane and water. The dichloromethane extracts were dried (sodium sulphate) and concentrated i, vacuo to give 63.4 g of a yellow oil. Chromatography on silica gel with dichloromethane: hexanes (3:2) gave 21.3 g (40%) of diethyl 2-(2-bromo-4-fluorobenzyl) malonate as a colourless oil. (A second fraction, 11.5 g, containing a minor impurity was obtained and could be used without further purification); NMR (CDCl$_3$); δ7.21–7.31 (m, 2H, Ar), 6.90–6.97 (m, 1H, Ar), 4.11–4.21 (m, 4H, 2X CH$_2$), 3.77 (t, 1H, CH), 3.30 (d, 2H. CH$_2$),1.22 (t, 6H, 2X CH$_3$).

c) Preparation of 3-(2-Bromo-4-Fluorophenyl) Propionic Acid A mixture of diethyl 2-(2-bromo-4-fluorobenzyl) malonate (31.8 g, 0.09 mol) and potassium hydroxide (10.3 g, 0.18 mol) in water (200 ml) was refluxed for 4.5 h. The mixture was concentrated in vacuo to remove the ethanol. To the resulting solution was added concentrated sulphuric acid (15.7 ml, 0.29 mol) and the mixture was refluxed for 18 h. The reaction mixture was chilled in an ice bath and the resulting solid was filtered, washed with water, and air dried to give 20.6 g (91%) of crude 3-(2-bromo-4-fluorophenyl) propionic acid. This material was used without further purification.

d) Preparation of(E)-2-(4-Bromo-6-Fluoro-1-Indanylidene)Acetamide

The above compound was prepared from 3-(2-bromo-4-fluorophenyl) propionic acid (19.6 g, 0.08 mol) by methods analagous to those described in Examples 1c–1 g and 2 via the following intermediates:

(i) 4-Bromo-6-Fluoro-1-indanone. Recrystallization of an 0.8 g sample from hexanes gave 0.54 g of 4-bromo-6-fluoro-1-indanone as a white solid: mp 129°–131° C.

(ii) Ethyl 2-(4-Bromo-6-Fluoro-1-Hydroxy-1-Indanyl) Acetate.

Chromatography on silica gel using hexanes:ethyl acetate (4: 1) gave 14. 1 g (70%) ethyl 2-(4-bromo-6-fluoro-1-hydroxy-1-indanyl)acetate as a pale yellow oil; NMR (CDCl$_3$): a 6.98–7.19 (m, 2H, Ar), 4.21 (q, 2H, CH$_2$CH$_3$), 3.04 (m, 1H, CH$_2$), 2.74 (m, 3H, CH$_2$'s), 2.31 (m, 2H, CH$_2$), 1.28 (t, 3H, CH$_3$).

(iii) 2-(4-Bromo-6-Fluoro-1-Hydroxyl-1-indanyl)Acetic Acid. Used immediately without further purification.

(iv) (E)-2-(4-Bromo-6-Fluoro-1-Indanylidene)Acetic Acid. Used without further purification.

(v) (E)-2-(4-Bromo-6-Fluoro-1-Indanylidene)Acetyl Chloride. Used without further purification.

Chromatography of the final product on silica gel with ethyl acetate: hexanes (7:3) as eluent and trituration of the resulting solid with pentane gave 1.4 g (47%) of (E)-2-(4-bromo-6-fluoro-1-indanylidene) acetamide as a white solid: mp 183°–185° C.; NMR (DMSO-d$_6$): δ7.54 (dd, 1H, Ar), 7.37 (m, 2H, Ar and NH$_2$), 6.98 (br s, 1H, NH$_2$), 6.39 (t, 1H, =CH), 3.17–3.22, 2.86–3.00 (2m's, 4H, 2XCH$_2$).

EXAMPLE 8

Preparation of (E)-2-(4-Chloro-6-methyl-1-indanylidene) acetamide

The above compound was prepared from 2-chloro-4-methylphenol (50.0 g, 0.35 mol, Aldrich) by methods analagous to those described in Examples 6a, 6b, 4b, 4c, 1c–1g and 2 via the following intermediates:

(i) 2-Chloro-4-Methylphenyl Trifluoromethanesulphonate. Chromatography on silica gel with hexanes as eluent gave 58.2 g (61%) of 2-chloro-4-methylphenyl trifluoromethanesulfonate as a colourless oil. NMR (DMSO-d$_6$); δ7.6 (s, 1H, Ar), 7.5(d, 1H, J=8.95 Hz, Ar), 7.3(d, 1H, J=8.95 Hz, Ar), 3.95(s,3H).

(ii) (E)-Ethyl 3-(2-Chloro-4-Methylphenyl) Acrylate. Chromatography on silica gel using hexanes:ethyl acetate (95:5) as eluent gave 24.1 g (70% yield) of pure (E)-ethyl 3-(2-chloro-4-methylphenyl) acrylate. NMR (DMSO-d$_6$): δ7.89 (d, 1H, CH=, J=16.0 Hz), 7.85 (d, 1H, J=8.2 Hz, ArH), 7.35 (s, 1H, Ar), 7.21 (d, 1H, J=8.2 Hz), 6.67 (d, CH=, J=16.0 Hz), 4.21 (q, 2H, J=7.1 Hz), 2.32(s,3H), 1.27(t, 3H, J=7 Hz).

(iii) Ethyl 3-(2-Chloro-4-Methylphenyl) Propionate. Chromatography on silica gel with hexanes: ethyl acetate (98:2) as eluent to give 29.10 g of ethyl 3-(2-chloro-4-methylphenyl) propionate as a colourless oil: NMR (CDCl$_3$); δ7.03–7.24 (m, 3H, Ar), 4.13 (q, 2H, CH$_2$), 2.93 (t, 2H, CH$_2$), 2.60 (t, 2H, CH$_2$), 2.27(s, 3H, CH$_3$), 1.17(t, 3H, CH$_3$).

(iv) 3-(2-Chloro-4-Methylphenyl) Propionic Acid. Used without purification; NMR (DMSO-d$_6$); δ12.2(s, 1H), 7.05–7.25 (m, 3H, As), 2.89 (t, 2H, CH$_2$), 2.75 (t, 2H, CH$_2$), 2.27(s, 1H).

(v) 4-Chloro-6-Methyl-1-indanone. Chromatography on silica gel with hexanes: ethyl acetate (99:1–95:5 gradient) as eluent gave 14.12 g (64%) of 4-chloro-6-methyl-1-indanone. NMR (DMSO-d$_6$): δ7.56 (s, 1H, As), 7.37(s, 1H, As), 2.96 ( m, 2H, CH$_2$), 2.64(m, 2H, CH$_2$), 2.35(s, 3H).

(vi) Preparation of Ethyl 2-(4-Chloro-6-Methyl-1-Hydroxy-1-Indanyl) Acetate. Chromatography on silica gel using hexanes:ethyl acetate (8:2) as eluent gave 6.36 g of ethyl 2-(4-chloro-6-methyl-1-hydroxy-1-indanyl)acetate as a yellow oil and 6.54 g of recovered starting material. The recovered starting material was resubmitted to the identical reaction conditions. Work up and chromatography as before gave 6.4 g of ethyl 2-(4-chloro-6-methyl-1-hydroxy-1-indanyl) acetate for a combined yield of 12.76 g (86%) as a colourless oil; NMR (DMSO): δ7.09 (s, 2H, Ar), 5.37 (br s, 1H, OH), 4.0 (m, 2H, CH$_2$CH$_3$), 2.6–2.95 (m, 4H), 4–2.6 (m, 1H), 2.28 (s, 3H), 2.0–2.2 (m, 1H), 1.08 (t, 3H, CH$_3$).

(vii) 2-(4-Chloro-6-Methyl-1-Hydroxy-1-indanyl)Acetic Acid. Used immediately without further purification.

(viii) (E)-2-(4-Chloro-6-Methyl-1-Indanylidene)Acetic Acid. Used without further purification.

(ix) (E)-2-(4-Chloro-6-Methyl-1-Indanylidene)Acetyl Chloride. Used without further purification.

Chromatography of the final product on silica gel with ethyl acetate: hexanes (1:1–3:1 gradient) as eluent provided 2.01 g (69%) of (E)-2-(4-Chloro-6-Methyl-1-Indanylidene) Acetamide as a white solid: mp 213°–215° C.; NMR (DMSO-d$_6$): δ 7.35 (br s, 1H, NH), 7.33 (s, 1H, Ar), 7.29 (s, 1H, Ar), 6.93 (br s, 1H, NH$_2$), 6.41 (t, 1H, =CH, J=2.6 Hz), 3.17–3.22, 2.90–2.97 (2m's, 4H, 2XCH$_2$), 2.35(s, 1H, CH$_3$).

Pharmaceutical Compositions

In the following composition Examples, the "Active Ingredient" may be any compound of formula (I) or base salt, acid addition salt, or other physiologically functional derivative thereof, for example, compounds of Examples 1 to 8.

EXAMPLE 9

Tablet Compositions

The following compositions A, B and C are prepared by wet granulation of the ingredients with a solution of povidone, followed by addition of magnesium stearate and compression.

| Composition A | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |

| Composition B | mg/tablet | mg/tablet |
|---|---|---|
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |

| Composition C | mg/tablet |
|---|---|
| Active ingredient | 100 |
| Lactose | 200 |
| Starch | 50 |
| Povidone | 5 |
| Magnesium Stearate | 4 |
| | 359 |

The following compositions, D and E, are prepared by direct compression of the admixed ingredients. The lactose in composition E is of the direct compression type (Dairy Crest—"Zeparox").

| | mg/tablet |
|---|---|
| Composition D | |
| Active ingredient | 250 |
| Pregelatinized Starch NF15 | 150 |
| | 400 |
| Composition E | |
| Active ingredient | 250 |
| Lactose | 150 |
| Avicel | 100 |
| | 500 |

Composition F (Controlled Release Formulation)

The composition is prepared by wet granulation of the ingredients (below) with a solution of povidone followed by the addition of magnesium stearate and compression.

| | | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P. | 28 |
| (e) | Magnesium Stearate | 7 |
| | | 700 |

EXAMPLE 10

Capsule Compositions

Composition A

A capsule composition is prepared by admixing the ingredients of Composition D in Example 68 above and filling into a two-part hard gelatin capsule. Composition B (infra) is prepared in a similar manner.

| | mg/capsule |
|---|---|
| Composition B | |
| (a) Active ingredient | 250 |
| (b) Lactose B.P. | 143 |
| (c) Sodium Starch Glycollate | 25 |
| (d) Magnesium Stearate | 2 |
| | 420 |
| Composition C | |
| (a) Active ingredient | 250 |
| (b) Macrogol 4000 B.P. | 350 |
| | 600 |
| Composition D | |
| (a) Active ingredient | 250 |
| (b) Lecithin | 100 |
| (c) Arachis Oil | 100 |
| | 450 |

Capsules of composition D are prepared by dispersing the active ingredient in the lecithin and arachis oil and filling the dispersion into soft, elastic gelatin capsules.

Composition E

| | mg/capsule |
|---|---|
| (a) Active ingredient | 100 |
| (b) Lactose | 300 |
| (c) Magnesium Stearate | 2 |
| (d) Sodium Lauryl Sulphate | 2 |
| (e) Sodium Starch Glycollate | 50 |
| (f) Talc, USP | 25 |
| | 479 |

A capsule composition is prepared by micronizing the active ingredient using a GEM-T Type 1047 Jet Mill and admixing with the remaining ingredients of Composition E and filling into a two-part hard gelatin capsule.

Composition F (Controlled Release Capsule)

The following controlled release capsule composition is prepared by extruding ingredients a, b and c using an extruder, followed by spheronization of the extrudate and drying. The dried pellets are then coated with release-controlling membrane (d) and filled into a two-piece, hard gelatin capsule.

| | mg/capsule |
|---|---|
| (a) Active ingredient | 250 |
| (b) Microcrystalline Cellulose | 125 |
| (c) Lactose B.P. | 125 |
| (d) Ethyl Cellulose | 13 |
| | 513 |

EXAMPLE 11

| Injectable Composition | |
|---|---|
| Active ingredient | 0.200 g |
| 95% Ethanol and PEG 400, 1:1 ratio | |
| Sterile water | q.s. to 10 ml |

The active ingredient is dissolved in 95% Ethanol and PEG 400 (1:1). The batch is then made up to volume with the water and filtered through a sterile micropore filter into a sterile 10 ml amber glass vial (type 1) and sealed with sterile closures and overseals.

EXAMPLE 12

| Syrup | |
|---|---|
| Active ingredient | 0.25 g |
| Sorbitol Solution | 1.50 g |
| Glycerol | 2.00 g |
| Sodium Benzoate | 0.005 g |
| Flavour, Peach 17.42.3169 | 0.0125 ml |
| Purified Water | q.s. to 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 13

| Suppository | mg/suppository |
|---|---|
| Active ingredient | 250 |
| Hard Fat, B.P. (Witepsol H15 - Dynamit NoBel) | 1770 |
| | 2020 |

One-fifth of the Witepsol H15 is melted in a steam-jacketed pan at 45° C. maximum. The active ingredient is sifted through a 200 μM sieve and added to the molten base with mixing, using a Silverson fitted with a cutting head, until smooth dispersion is achieved. Maintaining the mixture at 45° C., the remaining Witepsol H15 is added to the suspension and stirred to ensure a homogenous mix. The entire suspension is passed through a 250 μM stainless steel screen and, with continuous stirring, is allowed to cool to 40° C. At a temperature of 38° C. to 40° C., 2.02 g of the mixture is filled into suitable, 2 ml plastic moulds. The suppositories are allowed to cool to room temperature.

EXAMPLE 14

| Pessaries | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE 15

Antiinflammatory Activity

The compounds of formula (I) possess anti-inflammatory activity as demonstrated using a modification of the standard carrageenan pleurisy assay as described by R. Vinegar, J. F., Traux, and J. L. Selph (*Pro. Soc. Exp. Biol. Med* 143:711–714, 1973). The rats used in these experiments were Lewis males, weighing 160–180 g, assigned to groups consisting of 5 animals. Test compounds were given to fasted rats by oral gavage 0.5 hr prior to intrapleural injection of 50 μg carrageenan. After 4 hr, the pleural exudate was collected and the edema volume and cell number were determined. $ED_{50}$ values were estimated by linear regression analysis, and represent the doses at which a given drug produced 50% inhibition of carrageenan-induced cell accumulation and edema formation within the rat pleura.

EXAMPLE 16

| Compound of Example No. | p.o. $ED_{50}$, mg/kg | |
|---|---|---|
| | Cells | Edema |
| 1 | 8 | 5 |
| 2 | 11 | 11 |
| 3 | 25 | 20 |
| 6 | >25 | >25 |
| 7 | >20 | >20 |
| 8 | >25 | >25 |

Mild Analgesia

The compounds of formula (I) and (Ia) possess mild analgesic activity as demonstrated using a modification of the trypsin-induced rat hind limb hyperalgesic assay as described by R. Vinegar, J. F. Truax, J. L. Selph and P. R. Johnston (*J. Pharmacol. Meth.*, 23:51–61, 1990). The rats used in these studies were Lewis male, weighing 160–180 g. and assigned to groups consisting of 5–6 animals. Test compounds were given to fasted rats by oral gavage 0.5 hours prior to the subplantar injection of 250 μg trypsin in one hind limb. One hour later the rats were evaluated for hyperalgesia using a F-shaped mechanical force clamp on the injected hind limb metatarsal area. Latency (seconds) to the algesic response (vocalisation or flight) was determined, with 4 seconds being the maximum latency allowed. $ED_{50}$ values were estimated by linear regression analysis and represent the dose at which a given drug extended the latency response to produce 50% inhibition using the formula:

(4 sec.–Control Latency)–(4 sec.–Test Latency)/4 sec.–Control Latency×100.

| Compound of Example No. | p.o. $ED_{50}$, mg/kg |
|---|---|
| 1 | 2 |
| 2 | 4 |
| 3 | 4 |
| 6 | >10 |

Strong Analgesia

The compounds of formula (I) and (Ia) possess strong analgesic activity as demonstrated using the phalanges algesic assay [a modification of the trypsin-induced rat hind limb hyperalgesic assay as described by R. Vinegar, I. F. Truax, I. L. Selph and P. R. Johnston (*J. Pharmacol. Meth.* 23:51–61, 1990)]. The rats used in these studies were Lewis male weighing 160–180 g and assigned to groups of 5–6 animals. The phalanges algesic assay is an algesic test (no hyperalgesia). Test compounds were given to fasted rats by oral gavage. One hour later an F-shaped mechanical force clamp was applied to the phalanges of one hind limb which initiated an algesic response (vocalisation or flight). Latency (seconds) to the algesic response was determined with 3 seconds maximum allowed time. $ED_{50}$ values were estimated by linear regression analysis and represent the dose at which a given compound extended the latency response to produce 50% inhibition using the formula:

(3 sec.–Control Latency)–(3 sec.–Test Latency)/3 sec.–Control Latency×100.

| Compound of Example No. | p.o. $ED_{50}$, mg/kg |
|---|---|
| 1 | 60 |
| 2 | 30 |
| 3 | >45 |
| 6 | >45 |
| 7 | >45 |
| 8 | Inactive at 45 |

We claim:
1. A compound of the formula (I):

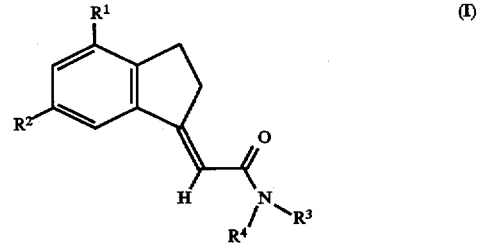

wherein $R^1$ and $R^2$ are independently selected from chloro, fluoro, bromo, $C_{1-6}$ alkyl, $C_{1-6}$ alkoxy or $C_{1-6}$ haloalkyl provided that both $R^1$ and $R^2$ are not fluoro; $R^3$ and $R^4$ are independently selected from hydrogen and ($C_{1-6}$ alkyl; or a pharmaceutically acceptable salt, solvate, or ester thereof.

2. A compound as claimed in claim 1 wherein at least one of $R^1$ and $R^2$ is chloro.

3. A compound of formula (1A)

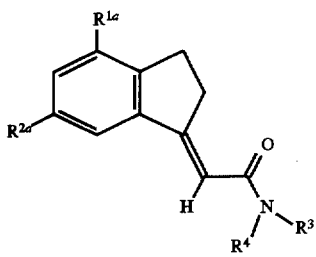
(IA)

wherein $R^{1a}$ is chloro, $R^{2a}$ is chloro, fluoro, bromo or methyl, and $R^3$ and $R^4$ are independently selected from hydrogen, methyl and ethyl; or a pharmaceutically acceptable salt, solvate or ester thereof.

4. A compound as claimed in claim 1 which is;

(E)-2-(4-chloro-6-fluoro-1-indanylidene)-N-methylacetamide;

(E)-2-(4-chloro-6-fluoro-1-indanylidene)acetamide;

(E)-2-(4,6-dichloro-1-indanylidene)acetamide;

(E)-2-(6-fluoro-4-methyl-1-indanylidene)acetamide;

(E)-2-(6-fluoro-4-methyl-1-indanylidene)-N-methylacetamide;

(E)-2-(6-chloro-4-fluoro-1-indanylidene)acetamide;

(E)-2-(4-bromo-6-fluoro-1-indanylidene)acetamide; or (E)-2-(4-chloro-6-methyl-1-indanylidene)acetamide.

or a pharmaceutically acceptable salt, solvate or ester thereof.

5. A pharmaceutical composition comprising at least one compound of formula (I) as defined in claim 1 or a pharmaceutically acceptable salt, solvate or ester thereof, together with one or more pharmaceutically acceptable carriers therefor.

6. A method for the treatment of conditions associated with inflammation, arthritis or pain in a mammal which comprises administering to the mammal a therapeutically effective amount of a compound of formula (I) as defined in claim 1 or a pharmaceutically acceptable salt, solvate ester thereof.

7. A process for the preparation of a compound of formula (I) as defined in claim 1 which comprises either:

(a) reacting a compound of the formula (II):

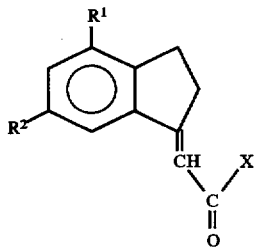
(II)

with an amine $NHR^3R^4$ wherein $R^1-R^4$ are as hereinbefore defined in claim 1 and X is a leaving group;

(b) by reaction of a compound of formula (III):

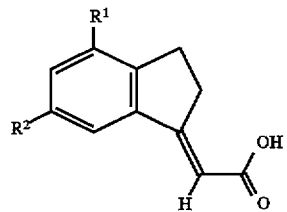
(III)

with a suitable coupling reagent followed by reaction with an amine $HNR^3R^4$ wherein $R^1-R^4$ are as defined in claim 1;

(c) by reacting the compound $R^3R^4NC(O)CH_2PO(OR^6)2$, wherein $R^3$ and $R^4$ are as defined in claim 1 and $R^6$ is $C_{1-6}$ alkyl with a base, followed by reaction with a compound of formula (V):

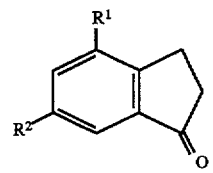
(V)

wherein $R^1$ and $R^2$ are as defined in claim 1.

(d) by reacting the compound $R^3R^4NC(O)CH_2P^{(+)}(Ph)_3Cl^{(-)}$, wherein $R^3$ and $R^4$ are as defined in claim 1 and Ph phenyl with a suitable base, followed by reaction with a compound of formula (V);

each of the above being optionally followed by (e) converting the compound of formula (I) so prepared into a salt, or ester thereof.

8. An intermediate of formula (II) or (III) as defined in claim 7 or of formula (IV)

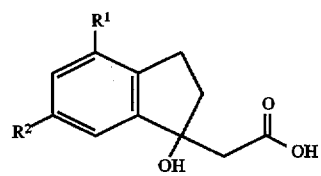
(IV)

wherein $R^1$ and $R^2$ are as defined in claim 7.

9. An intermediate selected from 2-(4-chloro-6-fluoro-1-hydroxy-1-indanyl)acetic acid (E)-2-(4-Chloro-6-fluoro-1-indanylidene)acetic acid (E)-2-(4-Chloro-6-fluoro-1-indanylidene)acetyl chloride 2-(4,6-Dichloro-1-hydroxy-1-indanyl)acetic acid (E)-(4,6-Dichloro-1-indanylidene)acetic acid (E)-2-(4,6-Dichloro-1-indanylidene)acetyl chloride 2-(6-Fluoro-1-hydroxy-4-methyl-1-indanyl)acetic acid (E)-2-(6-Fluoro-4-methyl-1-indanylidene)acetic acid (E)-2-(6-Fluoro-4-methyl-1-indanylidene)acetyl chloride 2-(6-Chloro-4-fluoro-1-hydroxy-1-indanyl)acetic acid (E)-2-(6-Chloro-4-fluoro-1-indanylidene)acetic acid (E)-2-(6-Chloro-4-fluoro-1-indanylidene)acetyl chloride 2-(4-Bromo-6-fluoro-1-hydroxy-1-indanylidene)acetic acid (E)-2-(4-Bromo-6-fluoro-1-indanylidene)acetic acid (E)-2-(4-Bromo-6-fluoro-1-indanyl)acetyl chloride 2-(4-Chloro-6-methyl-1-hydroxy-1-indanyl)acetic acid (E)-2-(4-Chloro-6-methyl-1-indanylidene)acetic acid and (E)-2-(4-Chloro-6-methyl-1-indanylidene)acetyl chloride.

* * * * *